United States Patent
Janoff et al.

(10) Patent No.: US 7,842,676 B2
(45) Date of Patent: Nov. 30, 2010

(54) FIXED RATIO DRUG COMBINATION TREATMENTS FOR SOLID TUMORS

(75) Inventors: Andrew Janoff, Yardley, PA (US); Lawrence Mayer, North Vancouver (CA); John Redman, Mullica Hills, NJ (US); Christine Swenson, Princeton Jct, NJ (US)

(73) Assignee: Celator Pharmaceuticals, Inc., Princeton, NJ (US)

( * ) Notice: Subject to any disclaimer, the term of this patent is extended or adjusted under 35 U.S.C. 154(b) by 888 days.

(21) Appl. No.: 11/586,215

(22) Filed: Oct. 25, 2006
(Under 37 CFR 1.47)

(65) Prior Publication Data

US 2009/0023680 A1    Jan. 22, 2009

Related U.S. Application Data

(60) Provisional application No. 60/730,199, filed on Oct. 25, 2005, provisional application No. 60/759,225, filed on Jan. 12, 2006.

(51) Int. Cl.
*A01N 43/04*     (2006.01)
*A61K 31/70*     (2006.01)
(52) U.S. Cl. ..................................... 514/50
(58) Field of Classification Search ............ 514/50
See application file for complete search history.

(56) References Cited

FOREIGN PATENT DOCUMENTS

WO    WO-03/028696    4/2003
WO    WO-2004/087115    10/2004

OTHER PUBLICATIONS

Reagan-Shaw, S., Nihal, M., Ahmad, N. (2007) Dose translation from animal to human studies revisited. The FASEB Journal, vol. 22, p. 659-661.*
Rougier, P. and coworkers. (1998) Randomised trial of irinotecan versus fluorouracil by continuous infustion after fluorouracil failure in patients with metastatic colorectal cancer. The Lancet, vol. 352, p. 1407-1412.*
Ansel, H.C., Allen, Jr., L.V., Popovich, N.G. (1999) Pharmaceutical Dosage Forms and Drug Delivery Systems. Published by Lippincott Williams & Wilkins, p. 23-26.*
"Development & Approval Process (Drugs)" from the U.S. Food and Drug Administration [online], [retrieved Mar. 18, 2010]. Retrieved from the internet <http://www.fda.gov/Drugs/DevelopmentApprovalProcess/default.htm>, last updated Oct. 27, 2009.*
"Clinical Cancer Advances 2006" published in the Journal of Clinical Oncology (2007), vol. 25, No. 1, p. 1-30.*
Raphaël, R., Yves, D., Giselle, C., Magali, M., Odile, C.M. (May 2005) Cancer treatment at home or in the hospital: what are the costs for French public health insurance: Findings of a comprehensive-cancer centre. Health Policy, vol. 72, p. 141-148.*
André, T., Louvet, C., Maindrault-Goebel, F., Couteau, C., Mabro, M., Lotz, J.P., Gilles-Amar, V., Krulik, M., Carola, E., Izrael, V., de Gramont, A. (1999) CPT-11 Addition to Bimonthly, High-dose Leucovorin and Bolus and Continuous-infusion 5-Fluorouracil for Pretreated Metastatic Colorectal Cancer. European J. of Cancer, vol. 35, p. 1343-1347.*
"Practice Guidelines in Oncology—v.3.2010" on "Colon Cancer" by the National Comprehensive Cancer Network. Published May 28, 2010.*
Allen et al., Science (Mar. 2004) 303:1818-1822.
Cao et al., Cancer Res (Jul. 2000) 60:3717-3721.
International Search Report for PCT/US2006/041832, date mailed on Apr. 24, 2007, 6 pages.
Litvak et al., Annals of Surgical Oncology (2002) 9(2):148-155.
Pitot et al., J. Clin. Oncol. (1997) 2910-2919.

* cited by examiner

*Primary Examiner*—Shaojia Anna Jiang
*Assistant Examiner*—Scarlett Goon
(74) *Attorney, Agent, or Firm*—Morrison & Foerster LLP

(57) ABSTRACT

Provided herein are methods for treating cancer by administering a pharmaceutical composition comprising a fixed, non-antagonistic molar ratio of irinotecan and floxuridine. Such methods are particularly useful in the treatment of cancer patients with advanced solid tumors.

7 Claims, 2 Drawing Sheets

FIGURE 1

CPX-1 Phase 1

| Patient # | Dose (units/m$^2$) | Primary | Best Response | Progression-free Survival (mos.) | Overall Survival (mos.) |
|---|---|---|---|---|---|
| 02-002 | 30 | Gastric | Prog | 1.6 | 1.6 |
| 02-001 | 30 | Renal | Prog | 1.8 | 12.7 |
| 01-001 | 30 | Breast | Stable | 3.6 | 15.2 |
| 01-002 | 30 | Breast | Stable | 3.6 | 6.9 |
| 01-004 | 60 | Colon | Prog | 0.8 | 3.5 |
| 01-005 | 60 | Esoph | Prog | 1.5 | 1.5 |
| 01-003 | 60 | Prostate | Stable | 3.5 | 8.9 |
| 02-003 | 60 | Gastric | Stable | 5.3 | 18.3+ |
| 02-004 | 100 | Colon | Stable | 3.5 | 16.7+ |
| 01-006 | 100 | Pancreatic | Stable | 3.4 | 8.7 |
| 01-007 | 100 | Ovarian | Stable | 16.4+ | 16.4+[a] |
| 02-005 | 100 | Colon | Stable | 12.0 | 16.2+ |
| 01-010 | 150 | Ovarian | Stable | 1.9+[b] | 13.9+[a] |
| 02-006 | 150 | Sarcoma | Stable | 4.2+[b] | 8.4 |
| 01-008 | 150 | NSCLC | PR | 6.3 | 8.7 |
| 02-007 | 150 | Colon | PR | 5.6 | 7.7 |
| 02-008 | 210 | Pancreatic | Stable | 7.2 | 12.5+ |
| 02-009 | 210 | Pancreatic | Prog | 1.8 | 12.3+ |
| 01-011 | 210 | Colon | Stable | 3.8 | 5.7 |
| 01-012 | 210 | Colon | Stable | 8.0 | 11.8+ |
| 02-012 | 210 | Colon | Prog | 1.9 | 3.1 |
| 01-016 | 210 | Osteosarcoma | Stable | 3.2 | 3.6 |
| 02-010 | 270 | Colon | N/A[c] | N/A | 3.2 |
| 02-011 | 270 | Sphenoid Sinus | Stable | 7.9 | 10.2+ |
| 01-014 | 270 | Esophageal | N/A[c] | N/A | 0.4 |
| 01-015 | 270 | Ovarian | N/A[c] | N/A[c] | 10.2+ |
| 01-017 | 210 | Colon | Stable | 5.6 | 7.2+ |
| 02-013 | 210 | Colon | Stable | 7.0+ | 7.0+ |
| 02-014 | 210 | Colors | Stable | 5.4 | 5.6+ |
| 02-015 | 210 | Colon | Stable | 3.8+ | 3.8+ |
| 02-016 | 210 | Colon | Stable | 2.9+ | 2.9+ |
| 01-018 | 210 | Colon | Stable | 2.9+ | 2.9+ |
| 01-019 | 210 | Colon | Prog | 2.0 | 2.6+ |

[a] The last evaluation not verified
[b] Patient withdrew consent; PFS censored
[c] Patients withdrawn before disease evaluation

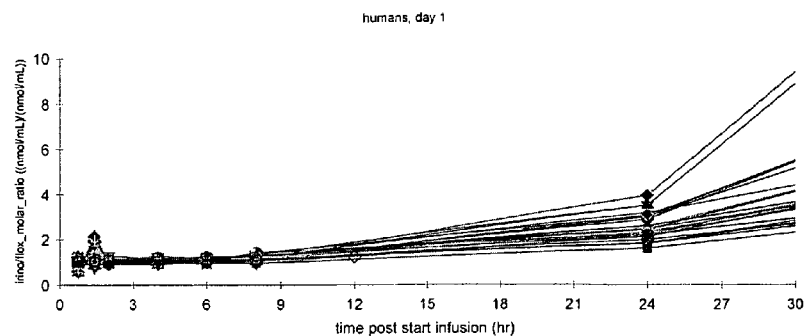

Molar ratio of irinotecan and floxuridine in the plasma of patients after iv infusion of 30-270 units/m2 of CPX-1. (concentrations determined by LC/MS/MS; Each line represents a single patient; N=26)

B.

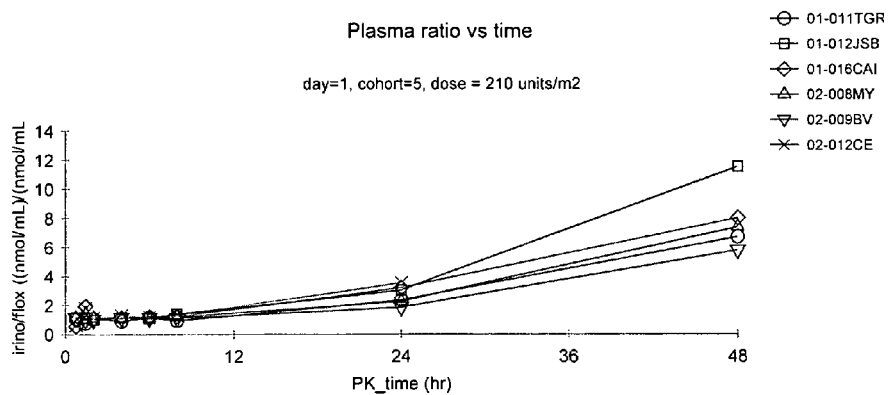

Molar ratio of irinotecan and floxuridine in the plasma of patients after iv infusion of 210 units/m2 of CPX-1. (concentrations determined by LC/MS/MS; Each line represents a single patient; N=6)

FIXED RATIO DRUG COMBINATION TREATMENTS FOR SOLID TUMORS

RELATED APPLICATIONS

This application claims the benefit of U.S. Provisional Application Ser. No. 60/730,199 filed Oct. 25, 2005 and U.S. Provisional Application Ser. No. 60/759,225, filed Jan. 12, 2006, each of which is incorporated herein by reference in its entirety.

TECHNICAL FIELD

The invention relates to methods for improved delivery and therapeutic effectiveness of a combination of therapeutic agents. More particularly, the inventions relates to delivery of a fixed ratio combination of floxuridine and irinotecan.

BACKGROUND ART

In vitro studies show that antitumor activity can be enhanced when cytotoxic drugs are used in combination. This has led, over the years, to the use of drug combinations in the clinic such that cytotoxic drug combinations are now standard in many forms of cancer chemotherapy. New anticancer drugs are typically first introduced in patients as single agents. After a maximum tolerated dose is determined for one agent, a second agent is added and the dose of one or both agents is adjusted on the basis of toxicity. The development of these combination regimens then is determined empirically on the basis of tolerability. However, in vitro, where the ratio of drugs used in combination can be controlled, it has been demonstrated that drug combinations providing synergy at one ratio may be simply additive or even antagonistic at other ratios (Mayer, L. D., et al., *Mol. Cancer Ther*. (2006) 5:1854-63; Chou, T-C., et al., *Adv. Enzyme Reg.* (1984) 22:27-55). When individual free drug is administered, each agent is handled differently by the body, resulting in varying distribution of the individual drugs to tumor sites which can result in drug ratios that are sub-optimal or ineffective. Consequently, in vitro synergistic activity of antineoplastic drugs often depends on specific drug ratios, and the in vivo activity of a combination therefore depends on maintaining a synergistic or additive ratio and avoiding antagonistic ratios. In this way, the development of a particular chemotherapeutic regimen can be based on the most efficacious ratio rather than empirically based on toxicity.

Fluoropyrimidines have been the cornerstone for the treatment of advanced colorectal cancer for over 30 years. 5-fluorouracil (5-FU) is regarded as standard systemic chemotherapy for this indication (Van Laar, J. A. M., et al., *Eur. J. Cancer* (1998) 34:296-306, Coutinho, A. K., et al., *Cancer Control* (2003) 10:224-238). Response to 5-FU appears to correlate with inhibition of thymidylate synthase activity more so than with incorporation of 5-FU into RNA. For this reason, intravenous floxuridine (the deoxyribonucleoside derivative of 5-FU) was investigated clinically in the early 1960's with the hypothesis that it would be therapeutically superior to 5-FU (Young, C. W., et al., *Cancer Chemother. Repts.* (1960) 6:17-20, Ansfield, F. J., et al., *Cancer Chemother. Repts.* (1963) 32:101-105, Reitemeier, R. J., et al., *Cancer Chemother. Repts.* (1965) 44:39-43, Eastern Cooperative Group, *JAMA* (1967) 200:101-118). These studies were conducted at leading oncology centers utilizing protocols that were state of the art at the time. Although Floxuridine clearly had activity in these studies, there was no clinical evidence that 5-FU and Floxuridine were meaningfully different. Floxuridine did not appear to be more active than 5-FU. 5-FU was less difficult to manufacture and more available so except for certain clinical investigations (Creaven, P. J., et al., *Cancer Chemother*. Pharmacol. (1994) 34:261-265), 5-FU has been used most often for systemic therapy. Floxuridine has demonstrated activity when administered as an hepatic arterial infusion in patients with hepatic metastases and is approved for this indication in the US (Anonymous, *J. Natl. Cancer Inst.* (1996) 88:252-258, Kemeny, N., et al., *Lancet Oncol*. (2001) 2:418-428).

Since the approval of irinotecan in 1996, the combination of irinotecan plus 5-FU has become a standard chemotherapy for first and second line treatment of metastatic colorectal cancer. The current most popular regimens are FOLFIRI as well as irinotecan as a single agent. Irinotecan is usually administered in two ways. In one regimen, 350 mg/m$^2$ irinotecan IV over 30 minutes administered every 21 days (Rougier P., et al., *J. Clin. Oncol.* (1997) 15:251-60). In another regimen, 125 mg/m$^2$ irinotecan IV over 90 minutes on days 1, 8, 15 and 22 repeated every 42 days (Pitot H. C. et al., *J. Clin. Oncol.* (1997) 2910-19). FOLFIRI usually contains about irinotecan 180 mg/m$^2$ IV, leucovorin (LV) 100-500 mg/m$^2$, and 5FU 2300-3000 mg/m$^2$ to be administered intravenously (IV) in 24 or 48 hour infusion or 400 mg/m$^2$ bolus followed by 600 mg/m$^2$ 22 hour infusion on days 1 and 2 repeated every two weeks. IFL contains irinotecan at 70 or 125 mg/m$^2$, LV 20-200 mg/m$^2$, and 5FU 450-500 mg/m$^2$ for IV bolus administration weekly for 4 weeks followed by two weeks rest. IFL is less favored because it is potentially more toxic and somewhat less active than FOLFIRI.

Despite the advantages associated with the use of combined drug cocktails, there are various drawbacks that limit their therapeutic use. For instance, administration of free drug cocktails often results in rapid clearance of one or all of the drugs before reaching the tumor site. If the individual drugs in the cocktail are only optimally effective within a narrow ratio to one another, a rapid clearance of one drug but not the other can reduce overall efficacy of the combination while often increasing toxicity. This can sometimes lead to increased toxicity as individual drug dosages are increased to achieve a greater therapeutic effect. Fluoropyrimidines such as 5-FU and floxuridine exhibit such rapid elimination and consequently attempts to improve activity have utilized longer infusion times to improve efficacy and toxicity profile of these agents. Typical times for such infusional administration can range from 24 hours or longer. Thus, drug delivery regimens that permit the sustained administration of an optimized drug combination ratio is highly desirable as its will permit reduced administration times without increasing the toxicity of the treatment. Such improvements in regimens also may permit higher overall doses being administered to the patient than would be possible with other regimens that are limited by toxicity.

DISCLOSURE OF THE INVENTION

In one aspect, provided herein is a method to treat cancer in a subject, said method comprising administering to said subject a pharmaceutical composition comprising a fixed, non-antagonistic molar ratio of irinotecan and floxuridine, wherein said fixed, non-antagonistic molar ratio is maintained in the plasma for at least about 4 hours. In another embodiment, the fixed non-antagonistic molar ratio is maintained for at least about 8 hours, at least about 16 hours, or at least about 24 hours. Typically, the irinotecan and floxuridine are stably associated with the delivery vehicle. In one embodiment, the delivery vehicle is a liposome.

In another aspect, provided herein is a method to treat cancer in a subject, said method comprising administering to said patient a pharmaceutical composition comprising a fixed, non-antagonistic molar ratio of irinotecan and floxuridine, wherein said composition is administered intravenously. In some embodiments, the pharmaceutical composition is administered in at least about 30 minutes and less than about 3 hours. In a specific embodiment, the pharmaceutical composition is administered in about 90 minutes.

In one aspect, provided herein is a method to treat cancer in a subject in need thereof, said method comprising administering to said patient a pharmaceutical composition comprising a fixed, non-antagonistic molar ratio of irinotecan and floxuridine, wherein floxuridine is administered at less than 0.001 moles/m$^2$/dose. In a specific embodiment, the floxuridine is administered at about 0.0003 moles/m$^2$/dose.

In another aspect, provided herein is a method to treat cancer in a subject in need thereof, said method comprising administering to said patient a pharmaceutical composition comprising a fixed, non-antagonistic molar ratio of irinotecan and floxuridine, wherein floxuridine is administered at less than 0.01 moles/m$^2$/month. In a specific embodiment, the floxuridine is administered at about 0.0006 moles/m$^2$/month.

In the methods provided herein, the fixed, non-antagonist molar ratio of irinotecan and floxuridine can be between about 5:1 and about 1:5. In a specific embodiment, the fixed, non-antagonist ratio of irinotecan:floxuridine is about 1:1. Typically, the fixed, non-antagonistic ratio of irinotecan and floxuridine is encapsulated in a liposome.

In some embodiments, the cancer is an advanced solid tumor. The advanced solid tumor can a gastric tumor, a renal tumor, a breast tumor, a colon tumor, an esophageal tumor, a prostate tumor, a pancreatic tumor, an ovarian tumor, an osteosarcoma, or a sphenoid sinus tumor. Sometimes, the cancer is a relapsed cancer. The subject can previously have undergone at least one anti-tumor regimen. Sometimes, the anti-tumor regimen is a multi-agent regimen.

BRIEF DESCRIPTION OF THE DRAWINGS

FIG. 1 shows the anti-tumor activity of CPX-1 in patients.

FIG. 2 shows the sustained fixed molar ratio of irinotecan:floxuridine in the plasma following administration of the liposomal-encapsulated irinotecan and floxuridine. A. Molar ratio of irinotecan and floxuridine in the plasma of patients after iv infusion of 30-270 units/m$^2$ of CPX-1 up to 24 hours. (concentrations determined by LC/MS/MS; Each line represents a single patient; N=26). B. Molar ratio of irinotecan and floxuridine in the plasma of patients after iv infusion of 210 units/m$^2$ of CPX-1 shown as plasma ratio over time. (concentrations determined by LC/MS/MS; Each line represents a single patient; N=6).

MODES OF CARRYING OUT THE INVENTION

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

For irinotecan and floxuridine, the non-antagonistic molar ratio range in vitro was between 5:1 and 1:5, where a molar ratio of 1:1 was found to be optimal (Mayer, L. D., et al., Mol. Cancer Ther. (2006) 5:1854-63). Thus, as used herein, the term "non-antagonistic molar ratio of irinotecan and floxuridine" refers to a molar range of irinotecan:floxuridine from between about 5:1 to about 1:5. In some embodiments, the non-antagonistic molar range is about 1:1 irinotecan:floxuridine.

Provided herein are methods to deliver non-antagonistic molar ratios of irinotecan and floxuridine to enhance tumor activity while providing the advantages of rapid administration and increasing doses with limiting toxic side effects. In brief, non-antagonistic ratios of chemotherapeutic agents were determined in vitro using screening techniques. If these same ratios are administered separately as free drug cocktails (e.g., conventional aqueous-based pharmaceutical formulations without liposome delivery), the ratio is not maintained because the drugs are distributed and eliminated independently of one another, resulting in a continuously changing ratio. Using co-encapsulated drugs in liposomes, the methods provided herein permit maintenance of the non-antagonistic ratio after administration for extended periods of time. The liposomal formulation delivers each drug in correct proportion by controlling the individual pharmacokinetics of each drug and thereby sustaining the non-antagonistic ratio.

Typically, sustained delivery requires a greater amount of a drug being administered in an effort to maintain a therapeutically effective level of the drug in the plasma and ultimately in the tumor. Such large doses are administered over a long period of time, often one or more days, requiring long hospital stays and/or reliance on prolonged infusion protocols that increase the risk of complications such as infection or pump malfunction. Another disadvantage is toxicity with the higher doses that may prevent an optimal plasma level from being achievable. Free drug cocktails are further disadvantaged when the drugs that are co-administered are only effective within a certain range of ratios of one another. For example, irinotecan and floxuridine molar can actually antagonize each other at certain irinotecan:floxuridine ratios (<5:1 and >1:5) depending on the tumor cell line.

CPX-1 is a liposomal formulation with a fixed 1:1 molar ratio of irinotecan HCl and floxuridine and has shown enhanced efficacy in cell culture and in in vivo models of colorectal carcinoma compared with the free drugs given as a cocktail and compared with individual liposomal drugs. See co-owned and co-pending U.S. Publication No. US 2004/0265368, filed Apr. 2, 2004. Any suitable source of irinotecan HCl and floxuridine can be employed. In one embodiment, the irinotecan HCl is (+)-7-ethyl-10-hydroxycamptothecine 10-(1,4' bipiperidine)-1'-carboxylate, monohydrochloride, trihydrate and the floxuridine is 2'-deoxy-5-fluorouridine.

Any suitable delivery vehicle can be employed that permits the sustained delivery of irinotecan:floxuridine combination in the fixed non-antagonistic molar ratio provided herein. In some embodiments, a liposomal formulation may be employed. The liposomes are designed for sustained delivery of the encapsulated drugs at a fixed ratio to a tumor site. In one embodiment, irinotecan and floxuridine are stably associated with the liposomes. Typically, the liposomes have a diameter of less than 300 nm, sometimes less than 200 nm. In one example, the nominal size of these liposomes is approximately 110 nm and sterilization is achieved by filtration through a 0.2 µm filter. In a specific embodiment, the liposome membrane is composed of distearoylphosphatidylcholine (DSPC), distearoylphosphatidylglycerol (DSPG) and cholesterol (CHOL) in a 7:2:1:molar ratio. In one instance, the liposomes are prepared by an water in oil derived liposome method and extruded liposomes are suspended in phosphate-buffered sucrose at pH 7.0. Any suitable means of encapsulating the drug combination in the liposomes can be employed. In a specific embodiment, irinotecan and floxuridine are encapsulated in the liposome using a copper gluconate/triethanolamine-based active loading procedure whereby irinotecan accumulates due to complexation inside preformed liposomes and floxuridine is passively encapsulated.

The methods provided herein are useful in any subject, particularly humans with cancer or advanced solid tumors. Cancer encompasses malignant cells with abnormal, uncontrolled growth. Such cells possess a number of characteristic properties such as uncontrolled proliferation, immortality, metastatic potential, rapid growth and proliferation rate, and certain typical morphological features. Often, cancer cells will be in the form of a tumor, but such cells may also exist alone within a mammal, or may be a non-tumorigenic cancer cell, such as a leukemia cell. A cell is identified as cancer by any of a number of ways, including, but not limited to, detecting the presence of a tumor or tumors (e.g., by clinical or radiological means), examining cells within a tumor or from another biological sample (e.g., from a tissue biopsy), measuring blood markers indicative of cancer (e.g., CA125, PAP, PSA, CEA, and the like), and/or detecting a genotype indicative of a cancer (e.g., TP53, ATM, and the like). The term "solid tumors" refers to tumors other than leukemias or lymphomas (i.e., cancers of the blood) that form solid masses of cancer cells. As used herein, the term "advanced solid tumors" refers to a malignant tumor that is metastatic or locally advanced and inoperable. Solid tumors can be of any origin including, but not limited to cancer of the adrenal gland, bladder, bone, brain, breast, cervix, colon, esophagus, gall bladder, ganglia, gastrointestinal tract, head and neck, heart, kidney, liver, lung, muscle, ovary, pancreas, parathyroid, prostate, rectum, salivary glands, sinus, skin, soft tissue, spleen, testis, thymus, thyroid, or uterus.

The methods disclosed herein provide for a sustained delivery of a non-antagonistic molar ratio of irinotecan and floxuridine. For example, the non-antagonistic molar ratio of irinotecan:floxuridine in the plasma is maintained for up to at least about 24, hours, at least about 16 hours, at least about 12 hours, at least about 8 hours, and often at least about 4 hours following a single administration of the drug combination. In addition, the sustained concentration of the liposomal encapsulated-drug combination in the plasma is greater than the drug concentration of the free cocktail drug combination in the plasma.

The methods also facilitate the administration of floxuridine at a significantly lower dose intensity than previously reported while maintaining its therapeutic effect. See Tables 1 and 2.

TABLE 1

Comparison of molar dose and dose intensity of Floxuridine or 5FU in combination with irinotecan

| | g/dose (m²) | mw | moles/ m²/ dose | moles/ m²/ month |
|---|---|---|---|---|
| CPX-1 270 units/m2 (floxuridine) | 0.0972 | 246.2 | 0.0004 | 0.0008 |
| CPX-1 210 units/m2 (floxuridine) | 0.0756 | 246.2 | 0.0003 | 0.0006 |

TABLE 1-continued

Comparison of molar dose and dose intensity of Floxuridine or 5FU in combination with irinotecan

| | g/dose (m²) | mw | moles/ m²/ dose | moles/ m²/ month |
|---|---|---|---|---|
| FOLFIRI (5FU) Tournigand | 3.2 | 130.08 | 0.0246 | 0.0492 |
| IFL (5FU) Saltz | 0.5 | 130.08 | 0.0038 | 0.0154 |
| FOLFIRI (5FU) NCCN/Italians | 1 | 130.08 | 0.0077 | 0.0154 |
| DeGramont Schedule (5FU/LV) | 1 | 130.08 | 0.0077 | 0.0154 |
| capecitabine | 5 | 359.35 | 0.0139 | 0.2922 |

TABLE 2

Comparison of molar dose and dose intensity of irinotecan in CPX-1 vs. FOLFIRI (Tournigand)

| | g/dose (m²) | mw | moles/ m²/ dose | moles/ m²/ month |
|---|---|---|---|---|
| CPX-1 (irinotecan) | 0.21 | 677.19 | 0.0003 | 0.0006 |
| FOLFIRI (5FU) Tournigand | 0.18 | 677.19 | 0.0003 | 0.0005 |

For example, the FOLFIRI regimen of a 5-FU and irinotecan requires a fluoropyrimidine (in this case 5-FU) dose intensity of 0.0246 moles/m²/dose or 0.0492 moles/m²/month. It should be noted that 5-FU and floxuridine are fluoropyrimidines that induce tumor cell death via the same active intermediate and have been shown to be equivalent clinically when administered at doses that are similar on a molar basis. The IFL regimen of 5FU, irinotecan and LV requires a fluoropyrimidine dose intensity of 0.0038 moles/m²/day or 0.0154 moles/m²/month. In contrast, the fluoropyrimidine (floxuridine in this case) dose intensity used during the administration of CPX-1 can be less than about 0.0035 moles/m²/dose, less than about 0.0025 moles/m²/dose, 0.0010 moles/m²/dose, or 0.005 moles/m²/dose of the irinotecan:floxuridine drug combination while maintaining therapeutic efficacy. Typically, only one dose is administered in a day. In a specific embodiment, the fluoropyrimidine dose intensity is about 0.0003 moles/m²/dose of the irinotecan:floxuridine drug combination. In some embodiments, the fluoropyrimidine dose intensity is less than about 0.0150 moles/m²/month, less than about 0.0100 moles/m²/month, less than about 0.0050 moles/m²/month, or less than about 0.0020 moles/m²/month. In a specific embodiment, the fluoropyrimidine dose intensity is about 0.0006 moles/m²/month of the irinotecan:floxuridine drug combination.

Using the methods provided herein, a fluoropyrimidine (i.e., floxuridine) is administered at doses that are less than when the drugs are administered individually in a conventional non-liposomal aqueous-based formulation while maintaining therapeutic efficacy.

The disclosed methods also provide a means of rapidly delivering a therapeutically effective dose of the drug combination irinotecan:floxuridine at a fixed molar ratio. The liposomal formulation of CPX-1 has the additional advantage of requiring a shorter (and thus more rapid) intravenous administration time than the current therapies. Typically, the liposome-encapsulated irinotecan:floxuridine drug combination can be administered to a patient by IV in at least about 30 minutes and less than about three hours. In one embodiment, the liposome-encapsulated irinotecan:floxuridine drug combination is administered IV over about 90 minutes. In contrast, other regimens employing free drug cocktails of irinotecan and floxuridine required at least 24 hours (Douillard J. Y. et al., *Lancet* (2000) 355:1041-47) and sometimes up to 48 hours of infusion (Tournigand C. et al., *Proc ASCO* (2000) 19:245a (Abstract 949); Tournigand C. et al., *J. Clin. Oncol.* (2004) 22(2):229-37). This is advantageous in, for example, lessening the hospital costs, improving the quality of life to the patient in avoiding a long hospital stay, avoiding pump complications, and reducing the chance of infection during such hospital stays.

The disclosed methods are therapeutically effective in treating relapsed cancer. A "relapsed cancer" refers to a cancer that has recurred following prior complete or partial remission in response to a prior treatment. Recurrence can be defined in any way, including a reappearance or re-growth of a tumor as detected by clinical, radiological, or biochemical assays, or by an increased level of a cancer marker. Prior treatments can include, but are not limited to chemotherapy, biological therapies, radiation therapy, and bone marrow transplantation.

In some embodiments, the patients treated with the methods provided herein are those that have previously been treated, failed or are resistant to other therapies. For example, patients can be treated with the methods provided herein after receiving or becoming resistant to any chemotherapy or biological therapy. In some cases, the patient have previously received a platinum-containing regimen. In one embodiment, the patient has previously received, FOLFIRI, FOLFOX (5-FU and oxaliplatin), or IFL. In a specific embodiment, the patient has previously been treated with irinotecan.

The methods disclosed herein can also be employed as a first line therapy for cancers that have not previously been treated.

Responses to the disclosed therapeutic methods include any clinically evident, positive change in tumor disease state. Such responses can include increases in overall survival and increases in progression-free survival. Disease responses are assessed by any suitable means. In one embodiment, disease is assessed using RECIST (Response Evaluation Criteria in Solid Tumors) criteria (Therasse, P., et al., *J. Natl Cancer Inst.* (2000) 92:205-16). Best response on study will be classified as outlined below: Complete Response (CR): disappearance of all clinical and radiological evidence of tumor. Partial Response (PR): at least a 30% decrease in the sum of the longest diameter of target lesions taking as reference the baseline sum of the longest diameters. Stable Disease (SD): steady state of disease. Neither sufficient shrinkage to qualify for PR nor sufficient increase to qualify for PD. Progressive Disease (PD): at least a 20% increase in the sum of the longest diameters of measured lesions taking as references the smallest sum of longest diameters recorded since the treatment started. Appearance of new lesions will also constitute progressive disease. In exceptional circumstances unequivocal progression of a non-measured lesion may be accepted as evidence of disease progression.

The pharmaceutical compositions provided herein are administered to any suitable subjects, preferably human subjects with cancer. Preferably, the pharmaceutical compositions of the present invention are administered intravenously. Dosage for the delivery vehicle formulations will depend on the ratio of drug to lipid and the administrating physician's opinion based on age, weight, and condition of the patient.

Pharmaceutical compositions comprising delivery vehicles of the invention are prepared according to standard techniques and may comprise water, buffered water, 0.9% saline, 0.3% glycine, 5% dextrose and the like, including glycoproteins for enhanced stability, such as albumin, lipoprotein, globulin, and the like. These compositions may be sterilized by conventional, well-known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, and the like. Additionally, the delivery vehicle suspension may include lipid-protective agents which protect lipids against free-radical and lipid-peroxidative damages on storage. Lipophilic free-radical quenchers, such as alpha-tocopherol and water-soluble iron-specific chelators, such as ferrioxamine, are suitable. Leucovorin may also be administered with compositions of the invention through standard techniques to enhance the life span of administered fluoropyrimidines.

The concentration of delivery vehicles in the pharmaceutical formulations can vary widely, such as from less than about 0.05%, usually at or at least about 2-5% to as much as 10 to 30% by weight and will be selected primarily by fluid volumes, viscosities, and the like, in accordance with the particular mode of administration selected. For example, the concentration may be increased to lower the fluid load associated with treatment. Alternatively, delivery vehicles composed of irritating lipids may be diluted to low concentrations to lessen inflammation at the site of administration. For diagnosis, the amount of delivery vehicles administered will depend upon the particular label used, the disease state being diagnosed and the judgment of the clinician.

EXAMPLE 1

Clinical Phase I Trial

The development of CPX-1 (Irinotecan HCl:Floxuridine) liposome injection was based on 1) defining a non-antagonistic ratio of the two active moieties, irinotecan HCl and floxuridine, using cell-based screening assays and 2) designing a liposomal drug carrier to maintain this ratio after intravenous administration. This ratio was not based on the empirically-derived regimens currently used for irinotecan HCl and fluoropyrimidines. Rather the ratio dependency of the antitumor effects of irinotecan and fluoropyrimidines provided the rationale for fixing these drugs in a carrier to improve on the therapeutic activity currently achieved with these combinations. It was anticipated that CPX-1 would provide an enhanced therapeutic effect in cancers that were sensitive to irinotecan and fluoropyrimidines. Preclinical data in human gastrointestinal tumor cell lines in vitro and in murine colorectal cancer models in vivo demonstrated the rationale for the chosen drug to drug ratio.

The primary objective of this study was to determine the recommended phase II dose of CPX-1 (defined as maximum tolerated dose (MTD) in this protocol) that can be given to patients with advanced solid tumors as an infusion on an every two week schedule. This study also evaluated the safety and dose-limiting toxicities (DLT) of CPX-1 and the pharmacokinetic parameters of CPX-1 administered in this schedule as well as determining preliminary efficacy information of CPX-1 administered in this schedule in patients with advanced solid tumors.

Physical, Chemical and Pharmaceutical Information

CPX-1 (Irinotecan HCl:Floxuridine) Liposome Injection was a liposomal formulation of a fixed combination of the antineoplastic drugs irinotecan HCL trihydrate ((+)-7-ethyl-10-hydroxycamptothecine 10-(1,4' bipiperidine)-1'-carboxylate, monohydrochloride, trihydrate) and floxuridine (2'-deoxy-5-fluorouridine) for intravenous infusion. The two drugs were contained within the liposome in a 1:1 molar ratio shown to have non-antagonistic activity in preclinical studies. The liposome membrane was composed of distearoylphosphatidylcholine (DSPC), distearoylphosphatidylglycerol (DSPG) and cholesterol (CHOL) in a 7:2:1:molar ratio. CPX-1 was intended for intravenous administration by slow infusion. CPX-1 (Irinotecan HCl:Floxuridine) Liposome Injection was provided as a sterile, pyrogen-free, pale blue-green, opaque dispersion in single-use vials. CPX-1 was stored frozen (−20° C.) and was thawed at room temperature for 60 minutes prior to dilution and administration. This dispersion was diluted in normal saline or dextrose for injection before intravenous administration to the patient.

Each single-use vial of CPX-1 (Irinotecan HCl:Floxuridine) Liposome Injection provided 25 mg of irinotecan HCl trihydrate and 9.1 mg of floxuridine. Each milliliter of the thawed drug product contained the ingredients as shown in the Table below.

TABLE 3

Components of CPX-1 liposomal injection

| Ingredient | mw | Amount per ml |
|---|---|---|
| Irinotecan HCl trihydrate | 677.19 | 5.0 mg |
| Floxuridine | 246.19 | 1.8 mg |
| Distearoylphosphatidylcholine (DSPC) | 790.16 | 29.2 mg |
| Distearoylphosphatidylglycerol (DSPG) | 801.07 | 8.5 mg |
| Cholesterol (CHOL) | 386.66 | 2.0 mg |
| Copper gluconate, USP | 453.85 | 4.3 mg |
| Triethanolamine, NF | 149.19 | <2.7 mg |
| Sucrose, NF | 342.3 | 102.7 mg |
| Sodium phosphate, monobasic, USP ($NaH_2PO_4$) | 120 | 1.7 mg |
| Sodium Phosphate Dibasic, USP ($Na^2HPO4$) | 141.96 | 7.0 mg |
| Water for Injection USP, q.s. | 18 | 1.0 ml |

All doses of CPX-1 described referred to the irinotecan HCl trihydrate and the floxuridine content delivered in the CPX-1 injections. For example, a dose of 50/18 mg/kg CPX-1 referred to 50 mg/kg of irinotecan HCl trihydrate plus 18 mg/kg floxuridine delivered as CPX-1. CPX-1 doses can also be referred to as units of CPX-1. One unit of CPX-1 contains 1 mg of irinotecan HCl trihydrate and 0.36 mg of floxuridine.

Clinical Studies

Starting Dose. For cytotoxic antineoplastic agents, the usual starting dose for the first trial in humans was calculated on the basis of body surface area (mg/m$^2$) and was generally given as 1/10th the $LD_{10}$ in rodents (if this dose was not severely toxic in non-rodents) or 1/3rd the "Toxic Dose Low" (the lowest dose which produced drug-induced pathologic alterations in hematologic, chemical, clinical or morphologic parameters) in the most sensitive species if double this dose was not lethal and did not cause severe, irreversible toxicity. An $LD_{10}$ for rodents was not identified for CPX-1 (Irinotecan HCl:Floxuridine) Liposome Injection. The highest doses tested (100 mg/kg irinotecan HCl in rats) did not cause any death. In dogs, the toxic dose low of CPX-1 (Irinotecan HCl:Floxuridine) Liposome Injection was 5 mg/kg irinotecan HCl (+1.8 mg/kg floxuridine) equivalent to 100 mg/m$^2$ irinotecan HCl. Double this dose was not lethal. From the toxicology information, the starting dose level for this phase I study was calculated to be CPX-1 33:12 mg/m$^2$. Arbitrarily, for dosing convenience, the starting dose was CPX-1 30:10.9 mg/m$^2$. In the study, one unit of CPX-1 contained 1 mg irinotecan and 0.36 mg floxuridine.

Schedule. The dosing schedule of every 14 days was chosen based on (1) precedent for irinotecan (and fluoropyrimidines), (2) animal pharmacokinetics for CPX-1, and (3) desire to avoid cumulative toxicities. Irinotecan schedules approved for use included irinotecan 125 mg/m$^2$ weekly×4, with two weeks rest and the "European schedule" of irinotecan 300-350 mg/m$^2$ every three weeks (the 300 mg/m$^2$ dose is suggested for age >70 years or performance status of 2). The FOLFIRI regimen (Tournigand, C., et al., *J. Clin. Oncol* (2004): 22:229-237), another frequently used irinotecan/5-FU/leucovorin regimen, was given every two weeks with an irinotecan dose of 180 mg/m$^2$.

Infusion Time. Acute infusion-associated reactions (e.g., flushing, shortness of breath, headache, chills, back pain, tightness in the chest and/or hypotension) have been noted in large clinical trials of patients receiving liposomal chemotherapeutic agents (Doxil®, Ortho Biotech Produces L.P. (2001), and DaunoXome®, Gilead Sciences, Inc. (2002) package inserts). In most patients, these reactions resolve over several hours to one day once the infusion is terminated. In some patients, the reaction resolves by slowing the infusion rate. The following table compares the amount of lipid in several liposome products and in CPX-1. A 90 minute infusion time was chosen based on this information.

TABLE 4

Amount of lipid in liposome products.

| Agent | Usual drug dose (mg/kg) | Lipid dose (mg/kg) | Infusion time (hours) | Lipid infusion rate (mg/kg/hr) |
|---|---|---|---|---|
| DaunoXome ® (40 mg/m$^2$) | 1.03 | 19.23 | 1 | 19.23 |
| Doxil ® (50 mg/m$^2$) | 1.28 | 10.26 | 1 | 10.26 |
| Myocet ® (60 mg/m$^2$) | 1.54 | 5.71 | 1 | 5.71 |
| CPX-1 | 3.21 | 25.55 | 1.5 | 16.86 |

Assumptions:

Doxil ® recommended to start at an infusion rate of 1 mg/min and then, if tolerated, the rate is increased to infuse over one hour.

Calculations are based on a 70 kg, 1.8 m$^2$ BSA patient.

CPX-1 dose assumed above would be the 125:45.5 mg/m$^2$ dose.

Patients had documented evidence of incurable, advanced, metastatic or recurrent cancer.

TABLE 5

Drug Administration

| Agent | Dose | Route | Duration | Schedule |
|---|---|---|---|---|
| CPX-1 | See dose level table below | IV | 90 minutes | Every 14 days |

Dose levels. The doses of CPX-1 were not escalated in individual patients. Dose were escalated in successive cohorts according to the following dose escalation scheme, based on toxicity.

TABLE 6

CPX-1 doses employed in patient cohorts.

| Cohort # | Factor (from modified Fibonacci Sequence) | Irinotecan Dose in CPX-1 (mg/m²) | Floxuridine Dose in CPX-1 (mg/m²) |
|---|---|---|---|
| 1 | 1 | 30 | 10.8 |
| 2 | 2 | 60 | 21.6 |
| 3 | 3.3 | 100 | 35.6 |
| 4 | 5 | 150 | 54.0 |
| 5 | 7 | 210 | 75.6 |
| 6 | 9 | 270 | 97.2 |

If necessary, subsequent doses were increased by a third for each cohort. The expectation, however, was that DLTs were likely to be seen by cohort 5, which received a dose that was slightly greater than irinotecan given on a 14 day schedule in FOLFIRI.

Drug Formulation. CPX-1 (Irinotecan HCl:Floxuridine) Liposome Injection was a liposomal formulation of a fixed ratio combination of the antineoplastic drugs irinotecan HCL trihydrate and floxuridine. The two drugs were present inside the liposome in a fixed 1:1 molar ratio. The liposome membrane was composed of distearylphosphatidylcholine (DSPC), distearylphosphatidylglycerol (DSPG) and cholesterol (CHOL) in a 7:2:1 molar ratio. These liposomes were prepared by an water-in-oil derived liposome method and were suspended in sucrose-phosphate-buffer at pH 7.0. The nominal size of these liposomes was approximately 100 nm; sterilization was achieved by filtration through a 0.22 μm filter.

CPX-1 was provided as a sterile, pyrogen-free, pale blue-green, opaque dispersion of 5 ml in amber glass, single-use vials. Doses of CPX-1 were referred to by the Irinotecan HCl trihydrate and the Floxuridine content delivered in the CPX-1 injections. For example, a dose of 50:18 mg/m² CPX-1 refers to 50 mg/m² of irinotecan HCl trihydrate plus 18 mg/m² floxuridine delivered as CPX-1.

Drug Administration. Treatment with CPX-1 (Irinotecan HCl:Floxuridine) Liposome Injection was administered by 90 minute intravenous infusion. The rationale for the length of infusion is outlined above. The infusion of CPX-1 (Irinotecan HCl:Floxuridine) Liposome Injection was performed through either a peripheral or central venous catheter, using an infusion pump to ensure that the drug was infused over the specified time period. Non-PVC containing administration sets, such as those that are polyethylene-lined were used. An in-line filter was not used.

Dose Limiting Toxicity (DLT) definition: DLT in a patient was defined using the NCI Common Terminology Criteria for Adverse Events v3.0 for toxicity occurring during the first cycle of therapy only. Dose limiting toxicity was defined as any grade 3 or 4 non-hematologic toxicity occurring during the first cycle of therapy (except for unpremedicated nausea or vomiting). Dose limiting hematologic toxicity was defined as absolute neutrophil count (ANC) <0.5×10⁹/L for >7 days, febrile neutropenia (defined as ANC <500×10⁹/L together with either fever >38.5 C or hospitalization for febrile neutropenia), platelet count <25×10⁹/L (with or without bleeding) or grade 3 thrombocytopenia (platelets <50×10⁹/L and >25×10⁹/L) associated with bleeding. For patients with liver metastases entering the study with ALT or AST from 3 to 5×ULN (grade 2 on CTCAE), grade 3 ALT or AST toxicity did not constitute a DLT.

Maximum Tolerated Dose (MTD) definition: The maximum tolerated dose (MTD) was defined as the dose at which there were fewer than one third of patients who experience a DLT, and this was the next lower dose from a cohort where a third or more experience a DLT.

If 0 of 3 or 4 patients at a given dose level experienced a DLT during therapy for a minimum of a 28 day treatment period, the next dose level was studied in another cohort of three or four patients.

If 1 of 3 (or 4) patients at a given dose level experiences a DLT, additional patients were added to a total of 6 that will be treated at the same dose level. Escalation will continue if one of the six patients experiences a DLT. If 2 or more patients experience a DLT in a given dose level, accrual to this level were discontinued. An additional three to twelve patients were entered at the prior dose level to confirm its adequacy as a phase II dose and to explore preliminary evidence for anti-tumor activity.

Pharmacokinetic Analysis

Plasma was analyzed for irinotecan and SN-38, and for floxuridine and 5 FU using validated and specific high performance liquid chromatographic mass spectrometric methods. Plasma concentration-time profiles were generated for irinotecan, SN-38, floxuridine, and 5-FU for each patient. Pharmacokinetic parameters were determined from the plasma concentration-time profile of all evaluable subjects. Using non-compartmental methods and WinNonlin™ Professional (Version 4.0 or higher), calculated pharmacokinetic parameters included, but were not limited to, the following:

| | |
|---|---|
| Cmax | Maximum observed concentration |
| Tmax | Time of occurrence of Cmax |
| λz | Elimination rate constant obtained from a linear regression of the natural log (ln) transformed concentration versus time data in the terminal phase (following dosing on Day 1 only) |
| t½ | Terminal half-life, calculated as ln(2)/λz |
| AUC(0-last) | Area under the plasma concentration-time curve from time zero to the time of the last post-dose quantifiable plasma concentration, obtained by the linear trapezoidal method |
| AUC(0-inf) | Area under the plasma concentration-time curve from time zero extrapolated to time infinity |
| CL | Systemic clearance computed as Dose/AUC(0-inf) (for irinotecan and floxuridine only) |

Descriptive statistics (mean, SD, CV %, median, min, and max) were used to summarize the plasma concentration and the PK parameters for each treatment cohort.

Results: 26 subjects (16M:10F), median age 54.5 y (21-72), all with prior therapy, enrolled in 6 cohorts with the 5th cohort expanded to 6 subjects. Diagnoses: 8 colorectal, 3 pancreatic, 3 ovarian, 2 breast, 2 gastric, 2 esophageal, 2 sarcomas, 1 renal cell, 1 prostate, 1 NSCLC and 1 sphenoid sinus. Seven subjects (4M:3F), median age 58 y (50-79), all with prior therapy and colorectal cancer enrolled in the extension phase of the study. See FIG. 1.

Almost all of the patients on the dose escalation phase of the study had advanced malignancies and extensive prior treatment. Consequently, our expectations for objective response and prolonged progression free survival (PFS>5 months) were low.

We observed two patients with objective partial responses. The first patient was a person with colon cancer whose response lasted 4.5 months. This subject presented with metastatic disease and was treated with surgical resection of the primary tumor, followed by irinotecan+oxaliplatin with shrinkage of liver metastases, attempted resection of residual liver lesions with discovery of persistent lymph node disease, and finally with capecitabine, all administered before entry into the Phase I study. This patient responded in spite of prior exposure to fluoropyrimidine and irinotecan.

The second patient had non-small cell lung cancer and responded for 3.0 months. This patient had received prior docetaxel, cisplatin, etoposide, and gefitinib. This type of cancer is traditionally not treated with fluoropyrimidines but may respond to irinotecan.

In addition, we have observed 9 patients with stable disease of 5 months or greater and there are three additional patients with ongoing progression free survivals (PFS) with the potential of exceeding 5 months duration in the near future. The majority of these patients have received extensive prior chemotherapy. The prior therapy received by these subjects are summarized in the table below:

TABLE 7

Prior Therapy received by patients

| Dose level U/m² | Tumor Type | PFS (mos) | Prior Chemotherapy |
|---|---|---|---|
| 60 | Gastric | 5.7 | capecitabine |
| 100 | Ovarian | 16.4+ | Docetaxel + carboplatin (adjuvant); gemcitabine |
| 100 | Colon | 11.8 | 5FU/LV, capecitabine, irinotecan, oxaliplatin, ALVAC-CEA |
| 210 | Pancreas | 7.4 | 5FU/LV, gemcitabine |
| 210 | Colon | 7.4 | 5FU/LV (adjuvant); FOLFOX; FOLFIRI |
| 210 | Colon* | 5.6 | 5FU/LV; XRT pelvis; FOLFOX + Bevacizumab; FOLFIRI; cetuximab; erlotinib |
| 210 | Colon* | 7.0+ | XRT; capecitabine |
| 210 | Colon* | 5.4 | XRT; 5FU/LV; FOLFOX, PTK787, ZK222584 |
| 270 | Sphenoid sinus tumor | 7.9 | Paclitaxel; cisplatin; carboplatin; gemcitabine; navelbine |

Safety: DLTs were observed at the 6th dose level: 4 subjects with DLTs: 3 diarrhea (one resulting in death due to dehydration/ARF) and one neutropenia. Other possibly related grade 3 and 4 events included one each of: grade 3 diarrhea, grade 3 vomiting, grade 3 neutropenia, grade 3 fatigue, grade 3 compression fracture and arthralgia and pulmonary embolism grade 4. PK: The pharmacokinetic analysis is shown in FIG. 2. In all 26 subjects analyzed to date, the 1:1 molar ratio of IRI to FLOX was maintained for 24 hours and metabolites 5-FU and SN-38 were present in the plasma. Below the results from the clinical trial were compared with published data from previous clinical trials.

TABLE 8

Comparison of PK of irinotecan when given as conventional drug or CPX-1

| Rx | dose mg/m² | N | IRINOTECAN Cmax ng/ml | IRINOTECAN AUC ng-h/ml | SN38 Cmax ng/ml | SN38 AUC ng-h/ml |
|---|---|---|---|---|---|---|
| Irinotecan data from Pitot HC et al. (2000) Clin Cancer Res 6: 2236-2244 | | | | | | |
| Irinotecan | 240 | 3 | 2,810 | 18,091 | 41 | 638 |
| | 340 | 6 | 3,392 | 22,998 | 56 | 714 |
| Data from clinical trial | | | | | | |
| CPX-1 | 30 | 4 | 13,782 | 285,601 | 5 | 226 |
| | 60 | 4 | 25,179 | 536,680 | 6 | 192 |
| | 100 | 4 | 52,773 | 1,011,357 | 14 | 500 |
| | 150 | 4 | 78,706 | 1,688,366 | 16 | 533 |
| | 210 | 6 | 93,552 | 1,831,229 | 24 | 730 |
| | 270 | 4 | 147,849 | 3,567,793 | 31 | 1,161 |

CPX1 represents a new approach to developing drug combinations in which drug ratios were pre-selected in vitro based on optimal antitumor activity and maintained systemically throughout pharmacokinetic control. Phase 2 studies are planned with a recommended dose of 210 unites (U)/m₂ of CPX-1.

Many modifications and variations of this invention can be made without departing from its spirit and scope, as will be apparent to those skilled in the art. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

Citation of the above publications or documents is not intended as an admission that any of the foregoing is pertinent prior art, nor does it constitute any admission as to the contents or date of these publications or documents. U.S. patents and other publications referenced herein are hereby incorporated by reference.

The invention claimed is:

1. A method to treat an advanced solid cancer in a human subject, said method comprising administering to said subject a pharmaceutical composition comprising a fixed, non-antagonistic molar ratio of irinotecan and floxuridine, wherein said fixed, non-antagonistic molar ratio is maintained in the plasma for at least about 4 hours, wherein said fixed, non-antagonistic molar ratio of irinotecan and floxuridine is about 1:1 and is encapsulated in liposomes, wherein each dose of the composition is administered intravenously to said human subject over a period of 30 minutes to three hours, wherein the dose contains less than 0.0004 moles/m² of floxuridine, and wherein floxuridine is administered at a level not greater than 0.0008 moles/m²/month, and wherein said advanced solid cancer is a gastric cancer, a renal cancer, a breast cancer, a colon cancer, an esophageal cancer, a prostate cancer, a pancreatic cancer, an ovarian cancer, an osteosarcoma, or a sphenoid sinus cancer.

2. The method of claim 1, wherein said fixed non-antagonistic molar ratio is maintained for at least about 8 hours.

3. The method of claim 1, wherein said fixed non-antagonistic molar ratio is maintained for at least about 16 hours.

4. The method of claim 1, wherein said treatment is a first line treatment or said subject has previously undergone at least one multi-agent anticancer regimen.

5. The method of claim 1, wherein each dose of said composition is administered in about 90 minutes.

6. The method of claim 1, wherein each dose of floxuridine contains 0.0003 moles/m².

7. The method of claim 1, wherein floxuridine is administered at 0.0006 moles/m²/month.

* * * * *